United States Patent [19]

Lynch

[11] 4,381,318

[45] Apr. 26, 1983

[54] MALTITOL CONTAINING GEL BASE SYSTEMS

[75] Inventor: Matthew J. Lynch, Wilmington, Del.

[73] Assignee: ICI Americas Inc., Wilmington, Del.

[21] Appl. No.: 289,465

[22] Filed: Aug. 3, 1981

Related U.S. Application Data

[63] Continuation-in-part of Ser. No. 222,300, Jan. 5, 1981.

[51] Int. Cl.³ ............................ A23L 1/09; A23L 1/04
[52] U.S. Cl. .................................. 426/658; 426/573; 127/38; 127/40
[58] Field of Search .................. 426/48, 658, 548; 127/38, 40

[56] References Cited

U.S. PATENT DOCUMENTS

| | | | |
|---|---|---|---|
| 3,538,230 | 11/1970 | Pader et al. | 424/50 |
| 3,689,637 | 9/1972 | Pader et al. | 424/50 |
| 4,024,239 | 5/1977 | Pader et al. | 424/49 |
| 4,154,867 | 5/1979 | Aldrich et al. | 426/658 |
| 4,181,712 | 1/1980 | Rialdi | 424/49 |
| 4,279,888 | 7/1981 | Suganuma et al. | 424/49 |
| 4,279,931 | 7/1981 | Verwaerde et al. | 426/658 |
| 4,303,641 | 12/1981 | De Wolf et al. | 424/49 |
| 4,314,990 | 2/1982 | Denny, Jr. et al. | 424/49 |

FOREIGN PATENT DOCUMENTS

| | | |
|---|---|---|
| 40-115120 | 7/1965 | Japan . |
| 2038832 | 7/1980 | United Kingdom . |

*Primary Examiner*—Jeanette M. Hunter

[57] ABSTRACT

Clear stable gels are made from hydrogenated maltose containing starch hydrolysates having 35–49% maltitol, 11–14% sorbitol, and minor amounts of higher saccharides by the addition of amorphous silica gelling agents. These gels are useful in formulating confections and food specialties.

2 Claims, No Drawings

MALTITOL CONTAINING GEL BASE SYSTEMS

This is a continuation-in-part of application Ser. No. 222,300 filed Jan. 5, 1981.

The invention is directed to maltitol syrups and edible gel bases made from these syrups containing a gelling agent. These compositions are particularly useful in formulating cosmetics, pharmaceuticals, confections and food specialties. In particular the invention is directed to the manufacture and use of syrups containing over 25% maltitol which are derived from the hydrogenation of maltose containing maltositol, dextrose and other saccharides. In cosmetic, pharmaceutical, confectionary and food preparations it is desirable because of high consumer acceptance to formulate the product as a stable clear transparent gel such as is sometimes used in toothpaste, cough gels, candy centers, cake decorations and ointments which are free of glycerine. The gel base is substantially free of sugar therefore it is a particularly useful vehicle for formulating toothpaste, candy and cake decorations where it's non-cariogenic properties are of value.

In the past transparent gels have been made from water, a gelling agent, specific actives, preservatives and a significant quantity of polyols such as sorbitol (USP), glycerine (USP), propylene glycol (USP) and others. Clear gels containing these polyols usually lose water when exposed to the atmosphere and forms crystals which are unsightly. Such loss of elegance is caused by the crystallization of certain polyols such as sorbitol and active ingredients contained within the gel especially when large quantities of sorbitol and glycerine are used. Furthermore, upon standing current gels loose fluidity as a result of surface evaporation. They are expensive to prepare as a result of the cost of the ingredients particularly the need to use glycerine.

Applicant has discovered that the use of certain hydrogenated maltose containing starch hydrolysate syrups in the preparation of clear transparent gels provide an economical solution to the preparation of gelled compositions which remain attractive over long periods of time even when exposed to atmospheric conditions. Furthermore, it has been discovered that maltitol syrups which result from starch hydrolysates are surprisingly resistant to the proliferation of airborne microorganisms such as mold when the total solids content is about 75% by weight and preferably about 80%.

It is an object therefore to provide for an aqueous maltitol containing hydrogenated maltose starch hydrolysate having a concentration of 25-94% by weight maltitol, 2-30% sorbitol (dry basis) and minor amounts of dextrines and noncariogenic low molecular weight polysaacharides which is resistant to the proliferation of microorganisms. Another object of the invention is to provide clear transparent non-crystallizing gel bases containing hydrogenated maltose hydrolysates comprising maltitol, sorbitol and higher saccharides wherein the weight ratio of maltitol to sorbitol is at least 2/1. Other objects of the invention are directed to cosmetic, pharmaceutical, confectionary and food preparations in the form of a clear transparent non-crystallizing gels and which are particularly useful in preparing toothpaste, cough gels, candy centers and cake decorating systems.

Maltitol is made by the hydrogenation of maltose which is the most common reducing disaccharide and is found in starch and other natural products. Starch is prepared from corn, wheat, rice, potatoes and tapioca amond other natural sources by conventional means well known to the art. High maltose containing starch derivatives are usually prepared by the enzymatic action of diastase (usually obtained from malt extract) on starch. Of particular interest are those maltose syrups which contain on a dry basis between 30 and 50% maltose, 5 to 15% dextrose and 30 to 40% higher saccharides. Syrups containing higher concentrations of maltose are commercially available and can be blended with other readily available maltose containing syrups obtained from natural products as a means for increasing the maltose concentration such that the syrup resulting from hydrogenation contains a maltitol/sorbitol weight ratio of no less than 2/1.

The hydrogenation of the maltose syrups is carried out according to well known procedures usually in the presence of nickel catalysts under base conditions according to the following preferred procedures as outlined in U.S. Pat. Nos. 2,968,680; 3,396,199; 3,341,609 and 3,691,100. Additional processes for preparing starch, starch hydrolysates and hexitols from such materials can be found in reissue patent 26,959; U.S. Pat Nos. 3,236,687; 3,305,395; 3,329,507; 3,519,482; 3,538,019; 3,565,765; 3,582,359; 3,616,220; 3,644,126; 3,670,035; 3,708,396; 3,962,465; 3,692;580; 3,974,032; 3,974,033 and 4,113,509.

A representative process for manufacturing a maltitol containing syrup for use in the invention is described in the following preparation. All proportions mentioned therein and in the examples following refer to percent or parts by weight.

Preparation I

A commercially available aqueous corn syrup containing on a dry basis 43.7% maltose, 5,8% dextrose and 50.5% higher saccharides is diluted with water to form a 60% solids solution as determined by high pressure liquid chromatography (HPLC) analysis. Higher saccharides are defined as all polysaccharides greater than disaccharides such as tri and tetrasaccharides. Up to nine maltose units have been observed by HPLC analysis, however, the major portion are tri and tetrasaccharides. This solution is further purified by passing it through a cationic exchange resin in the H+ form (Dualite C-25D) and thereafter further purified through an anionic exchange resin in the OH− form (Dualite ES561). This liquid is then further concentrated to 65% solids by the evaporation of water.

This diluted material is then hydrogenated in a continuous autoclave in the presence of a supported nickel catalyst at a 0.6% nickel/solids ratio in the presence of 0.05% calcium carbonate at 160° C. using an addition rate of 8.7-10 liters per hour of hydrogen at 1500-2000 psi.

The effluent is then again purified by filtration and passage through a cationic exchange and an anionic exchange resin as described above and thereafter concentrated to remove water.

This process yields when similar starting materials are use products containing on a dry basis 11-14% Sorbitol, 36-49% Maltitol, 41-47% higher saccharides and 0.01-0.10% reducing sugars in aqueous solutions containing 70-85% and preferably at least 75% by weight solids as determined by the N.F. XV (National Formulory XV, p. 261 of United States Pharmacopeia) method of analysis or the HPLC method adjusted to conform to the N.F. XV method.

Preparation II

An aqueous solution of N.F. maltose (National Formulory, Amer. Pharm. Ass., p. 664–665, 1946) containing 50% solids was hydrogenated according to a procedure outlined for Preparation I to produce a maltitol solution having 85.6–94.0% maltitol, 2–5% sorbitol, 2.1–2.6% higher saccharides, 0.013–0.24% reducing sugars calculated on a dry basis in aqueous solutions having 71–78% total solids.

Preparation III

A 50/50 blend of a material made according to Preparation I containing 19.8% water with the high maltitol composition as made in Preparation II containing 22.5% water and containing on a dry basis 94% maltitol, 5% sorbitol and 2.6% higher saccharides is made to form a maltitol syrup containing 53.52% maltitol, 7.6% sorbitol, 16.72% higher saccharides, 0.033% reducing sugars and 79% total solids.

Preparation IV

A syrup blend consisting of 7.5 parts Preparation III with 2.5 parts USP sorbitol comprising 53.2% sorbitol, 2.8% maltitol, 4.8% higher saccharides, 0.06% reducing sugar and 29.3% water can be made to provide a syrup containing 19% sorbitol, 40.84% maltitol, 13.74% higher saccharides and 0.39% reducing sugars and a 75% solids content. Such compositions have a maltitol/sorbitol ratio of 2/1 and are resistant to airborne mold growth.

Useful maltitol/sorbitol containing syrups are provided for use in the manufacture of clear gels where maltitol syrups containing at least 50% and preferably at least 80% maltitol are blended with sorbitol solutions containing lower concentration of maltitol.

Demonstration I

Maltitol syrup as prepared in Preparation I is diluted with water to total solid concentrations of 71, 72, 75 and 80% by weight and permitted to stand in open air. Syrups having concentrates of 71 and 72% support mold growth while the 75 and 80% concentrates remain clear.

In addition to the above described preparations the novel maltitol containing syrups can be made by first enriching maltose containing syrups derived from natural products with additional pure maltose before conducting the hydrogenation and purification steps.

Aqueous maltitol syrups made by these and other preparative processes usually have a total dissolved solids content of 60–85% by weight and can have an analysis when calculated on a dry basis (not including water content) as follows: Maltitol 25–94%, Sorbitol 2–30%, and reducing sugar 0.05–2% and higher saccharides.

The above-described maltitol syrups are useful in preparing clear stable transparent gels when combined with 5–10% gelling agent preferably amorphorous silica or its equivalent having an index of refraction in the range of 1.3–1.5, 10–40% water and minor amounts or preservatives, coloring agents, flavoring agents, pharmaceutically active compounds, germicides, antioxidants, and the like. In order that the gel be clear and transparent selected ingredients must be either completely soluble in the gel base or have a refractive index substantially close to that of the base formula. Furhermore, the ingredients must be so incorporated to prevent the inclusion of air bubbles. Other ingredients are limited to those which do not cause a substantial defraction of light before it passes completely through the gel. In many instances, it is difficult to predict the effect of one ingredient upon another in a formulation and their effect upon the transparency of the gel. In many cases a formulation with the desired appearance can only be found by making compositions for the intended purpose and varying the ingredient concentrations until a suitable appearance is obtained. It is critical to substantially match the refractive index of the gelling agent and in the case of this invention with the principal base gelling agent as well as any abrasives used in the case where a toothpaste is made. A preferred gelling agent is amorphous silica which has a refraction index of 1.46 or there about, an average particle size of 3–10 microns and a surface area in the range of 300–1000 square meters per gram. This value then becomes the fixed point which must be matched. A major advantage of the maltitol syrups is that they have a refractive index in the region of 1.491 depending upon the concentration of ingredients and water content. It is now possible to closely match refractive indexes by adding or subtracting water from an amorphous silica/maltitol syrup combination. When a refractive index of 1.46 is obtained a clear transparent stable gel is formed. Other polyols such as glycerine (refractive index 1.473) additional USP sorbitol solution (refractive index 1.459) may be blended with water and maltitol syrup to yield stable transparent gels. These other polyols may be required in certain instances to achieve special solvent effects for certain actives while retaining the transparent gel properties as long as the maltitol concentration in the system is maintained at a concentration of at least 25% (dry basis) and the maltitol/sorbitol weight ratio is at least 2/1. For reasons unknown the gels are not stable if the maltitol/sorbitol ratio is less than 2 because they crystalize and lose elegance and transparency.

While the gels of the invention are particularly useful in making transparent formulations with greater economy than previously obtainable they can be employed in preparing opaque formulations especially where the absence of cariogenic sugars is desirable. Such compositions are rather easy to make by comparison with clear transparent formulas because the solids dispersed therein need not have nearly matching refractive indexes.

Gel based compositions employing the maltitol syrups having 30–70% by weight maltitol and maltitol/sorbitol weight ratios no less than 2:1 are demonstrated but not limited to those of the following examples:

EXAMPLE 1

A clear stable gel base is prepared from the following ingredients:

| Ingredients | % by weight |
|---|---|
| Silica (Syloid ® 244 - amorphous 3 micron average particle size) | 10.0 |
| Maltitol syrup of Preparation I | 69.0 |
| Sodium benzoate (preservative) | 0.5 |
| Water | 21.0 |

These ingredients are blended by first dispersing sodium benzoate, maltitol syrup and amorphorous silica in water and thereafter homogenizing the mixture for a period of two minutes in a Versator type homogenizer produced by Cornell Manufacturing Company.

The gel has a refractive index of 1.46 and is stable at temperatures of 5° C.–50° C. for several months.

Further suitable gel formulations can be made as shown in Table 1.

TABLE I

| Example No. | Example 2-4 Ingredients (% by wt.) | |
|---|---|---|
| | Amorphous Silica (Syloid - 244) | Maltitol Syrup |
| 2 | 10 | 90 Prep. I |
| 3 | 10 | 90 Prep. III |
| 4 | 10 | 90 Prep. IV |

Base gels similar to those formulations described above can be employed to manufacture consumer products such as toothpaste, food products, ointments and pharmaceuticals by incorporating therewith additional active ingredients.

For example toothpastes both opaque and transparent can be formulated according to the Pader U.S. Pat. Nos. 3,538,230; 3,689,637 and 4,024,239 by adding to the gel compositions polishing agents such as anhydrous or dihydrated dicalcium phosphate, sodium metaphosphate, silica xerogel, silica aerogel, alumina trihydrate, percipitated chalk, calcium pyrophosphate and alpha alumina trihydrate in concentrations ranging from 10 to about 50% by weight of the toothpaste formulation. Most formulations include minor amounts of flavoring agents, foaming agents such as detergents and soaps, fluoride treating agents such as stannous fluoride, delusterants such as titanium dioxide, and germicides such as hexachlorophene. In general, satisfactory toothpastes are made by substituting for the polyol ingredients in the formulas described in the above cited patents a stable gel composition similar to that described in the above examples. Therefore, satisfactory toothpaste can be prepared which contain about 15-25% amorphous silicas or their equivalent, 50-75% maltitol syrup additional sweeteners and minor amounts of coloring agent, flavoring, surfactant, fluoride treatment, germicides and soaps.

The preparation of a toothpaste formulation is demonstrated but not limited to that of the following examples:

EXAMPLE 5

A clear gel toothpaste can be prepared by dispersing 67.1 parts of the maltitol syrup described in Preparation I with 7 parts of an amorphous silica gelling agent (Syloid ® 244 having an average particle size of 3 microns sold by Grace Chemical Co.), 14 parts amorphous silica abrasive (Syloid 63 having an average particle size of 10 microns) and 20.1 parts water. To this gel is added 0.3 parts carboxymethyl cellulose thickening agent, 1.5 parts sodium lauryl sulphate detergent, 0.081 parts sodium benzoate perservative, 0.2 parts saccharin artificial sweetener, 2.0 parts peppermint flavor oil and 0.1 parts red dye. These ingredients are mixed well in a blender and the deaireated and simultaneously homogenized under high shear mixing to produce good texture (short) and high gel strength.

EXAMPLE 6

Another example of a stable transparent toothpaste gel may be formulated by altering the polyol to achieve special solvent properties that may be required to solubilize a flavor with poor solubility. 67.1 parts of maltitol syrup described in Preparation II is blended with 7 parts of amorphous silica gelling agent (Syloid ® 244 having an average particle size of 3 microns sold by Grace Chemical Company), 14 parts amorphous silica abrasive (Syloid 63 having an average particle size of 10 microns) and 20.1 parts water to this gel is added 0.3 parts carboxymethyl cellulose thickening agent, 1.5 parts sodium lauryl sulfate detergent, 0.081 parts sodium benzoate perservative, 0.2 parts saccharin artificial sweetener, 2.0 parts peppermint flavor oil and 0.1 part suitable dye.

Procedure is the same as that used in Example 5.

EXAMPLE 7

Another example of a stable transparent toothpaste gel may be formulated using maltitol syrup described under Preparation III.

64.1 parts of maltitol syrup described in Preparation III with 7 parts of amorphous silica gelling agent (Syloid ® 244) having an average particle size of 3 microns sold by Grace Chemical Co.), 14 parts amorphous silica abrasive (Syloid 63 having an average particle size of 10 microns) and 23.1 parts water to this gel is added 0.3 parts carboxymethyl cellulose thickening agent, 1.5 parts sodium lauryl sulfate detergent, 0.081 parts sodium benzoate preservative, 0.2 parts saccharin artificial sweetner, 2.0 parts peppermint flavor oil and 0.1 part suitable dye.

Procedure is the same as that used in Example 5.

A gelled cough medicine which can be sold in a tube for children's use and which can be administered as a gel on a spoon with less chance of spilling is formulated but not limited to that in the following example:

EXAMPLE 8

A gelled cough medicine as prepared by dissolving 1 part sodium benzoate, 1.9 parts sodium saccharin, 1 part green dye and 1 part peppermint flavoring in 18.4 parts water. With high sheer agitation disperse 20 parts amorphous silica (Syloid 244), 61.4 parts maltitol syrup as described in Preparation I, and 0.2 parts dextromethorphan hydrobromide USP. The dispersion is homogenized under vacuum to remove air to form a transparent gel cough remedy. The formula may include other beneficial ingredients such as expectorants and antihistamines.

The maltitol gel of the invention can also be employed to form colored sweet tasting gels for food applications especially useful in candy centers and cake decorating. A composition similar to that shown in the following example can be used as a cake decoration or candy center.

EXAMPLE 9

A sweet tasting food gel can be made by adding 1 part U.S. Food Drug and Cosmetic red dye No. 33 to 18.2 parts water. This is then dissolved in 60.8 parts of a maltitol syrup described in Preparation I and thereafter thickened with 10% amorphous silica (Syloid ® 244) and thereafter homogenized under vacuum to form a clear transparent gel suitable for cake decoration and a candy filler. In addition it is advisable to include a preservative and alternative flavoring agents.

What is claimed is:

1. An aqueous maltitol containing syrup resistant to mold growth resulting from the hydrogenation of maltitol rich syrup which comprises 36-49% by weight maltitol, 11-14% by weight sorbitol, minor amounts of higher saccharides and reducing sugars when said ingredients are calculated on a dry basis said syrup having a total dissolved solids content of 75 to 85% by weight when calculated on a wet basis.

2. A composition of claim 1 having a total dissolved solids content of 75%-80% by weight.

* * * * *

UNITED STATES PATENT AND TRADEMARK OFFICE
CERTIFICATE OF CORRECTION

PATENT NO. : 4,381,318
DATED : April 26, 1983
INVENTOR(S) : Matthew J. Lynch

It is certified that error appears in the above-identified patent and that said Letters Patent are hereby corrected as shown below:

Column 2, line 35: "5,8%" should read --5.8%--

Column 3, line 62: "Furher-" should read --Further- --

Column 6, Claim 1, line 59 and 60: "hydrogenation of maltitol" should read --hydrogenation of maltose--.

Signed and Sealed this

Thirteenth Day of December 1983

[SEAL]

Attest:

Attesting Officer

GERALD J. MOSSINGHOFF

Commissioner of Patents and Trademarks